US006353110B1

United States Patent

(12) United States Patent
Devine et al.
(10) Patent No.: US 6,353,110 B1
(45) Date of Patent: Mar. 5, 2002

(54) ASYMMETRIC CONJUGATE ADDITION REACTION

(75) Inventors: Paul N. Devine, Lincroft; Richard D. Tillyer, Westfield, both of NJ (US); Richard M. Heid, Jr., Brooklyn, NY (US); David M. Tschaen, Holmdel, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/448,775

(22) Filed: Nov. 24, 1999

Related U.S. Application Data

(62) Division of application No. 09/115,493, filed on Jul. 14, 1998, now Pat. No. 6,022,972.

(60) Provisional application No. 60/087,039, filed on May 28, 1998, and provisional application No. 60/055,259, filed on Aug. 8, 1997.

(51) Int. Cl.[7] .............................................. C07D 403/06

(52) U.S. Cl. .................... 546/283.7; 546/301; 546/340; 546/341; 546/342

(58) Field of Search ............................. 546/283.7, 301, 546/340, 341, 342

(56) References Cited

U.S. PATENT DOCUMENTS 5,389,620 A 2/1995 Ishikawa et al.
5,714,479 A 2/1998 Ishikawa et al.

FOREIGN PATENT DOCUMENTS

EP 0526708 A1 6/1992
WO WO 93/08799 5/1993

OTHER PUBLICATIONS

Chemical Abstracts 124:175888, abstract of Leonard, Tetrahedron (1995), 51(47), pp. 12843–12858.

Chemical Abstracts 122:81251, abstract of Castle, Tetrahedron Letter (1994), 35(40), pp. 7455–7458.

Chemical Abstracts 117:47646, abstract of Christenson, Tetrahedron, (1992), 48(17), pp. 3623–3632.

Bemis, et al., Database Caplus On Stn., No. 129:81749, 1998.

Devine, et al., Database Caplus On Stn., No. 128:192553, 1998.

Tucker, et al., Database Caplus On Stn., No. 127:287702, 1997.

Meyers, et al., Database Caplus On Stn., No. 92:76692, 1980.

Meyers, et al., Database Caplus On Stn., No. 86:106450, 1977.

Meyers, et al., Database Caplus On Stn., No. 85:32335.

Levy, et al., Database Caplus On Stn., No. 69:96750, 1969.

J. Org. Chem., vol. 44, No. 13, Meyers et al. pp. 2250–2256, 1979.*

J. of American Chemical Society 97 :21, pp. 6266–6267, 1975.*

Tetrahedron Letters No. 30, pp. 2749–2752, 1979.*

* cited by examiner

*Primary Examiner*—Jane Fan
(74) *Attorney, Agent, or Firm*—Valerie J. Camara; Mark R. Daniel

(57) ABSTRACT

This invention relates to a key intermediate in the synthesis of an endothelin antagonist the synthesis of this key intermediate via an asymmetric conjugate addition reaction.

11 Claims, No Drawings

ASYMMETRIC CONJUGATE ADDITION REACTION

This is a division of application Ser. No. 09/115,493 now U.S. Pat. No. 6,022,973 filed Jul. 14, 1998 which claims benefit of Nos. 60/055,259 Aug. 8, 1997 and 60/087,039 May 28, 1998 under 119(c).

BACKGROUND OF THE INVENTION

The present invention relates to novel key intermediates in the synthesis of an endothelin antagonist and the method for preparing these key intermediates of Formula I.

Two endothelin receptor subtypes $ET_A$ and $ET_B$ are known. The compounds of the present invention possess high affinity to at least one of two receptor subtypes, responsible for the dilation of smooth muscle, such as blood vessels or in the trachea. The endothelin antagonist compounds of the present invention provide a new therapeutic potential, particularly for the treatment of hypertension, pulmonary hypertension, Raynaud's disease, acute renal failure, myocardial infarction, angina pectoris, cerebral infarction, cerebral vasospasm, arteriosclerosis, asthma, gastric ulcer, diabetes, restenosis, prostatauxe endotoxin shock, endotoxin-induced multiple organ failure or disseminated intravascular coagulation, and/or cyclosporin-induced renal failure or hypertension.

Endothelin is a polypeptide composed of amino acids, and it is produced by vascular endothelial cells of human or pig. Endothelin has a potent vasoconstrictor effect and a sustained and potent pressor action (Nature, 332, 411–415 (1988)).

Three endothelin isopeptides (endothelin-1, endothelin-2 and endothelin-3), which resemble one another in structure, exist in the bodies of animals including human, and these peptides have vasoconstriction and pressor effects (Proc. Natl. Acad, Sci, USA, 86, 2863–2867 (1989)).

As reported, the endothelin levels are clearly elevated in the blood of patients with essential hypertension, acute myocardial infarction, pulmonary hypertension, Raynaud's disease, diabetes or atherosclerosis, or in the washing fluids of the respiratory tract or the blood of patients with asthmaticus as compared with normal levels (Japan, J. Hypertension, 12, 79, (1989), J. Vascular medicine Biology, 2, 207 (1990), Diabetologia, 33, 306–310 (1990), J. Am. Med. Association, 264, 2868 (1990), and The Lancet, ii, 747–748 (1989) and ii, 1144–1147 (1990)).

Further, an increased sensitivity of the cerebral blood vessel to endothelin in an experimental model of cerebral vasospasm (Japan. Soc. Cereb. Blood Flow & Metabol., 1, 73 (1989)), an improved renal function by the endothelin antibody in an acute renal failure model (J. Clin, invest., 83, 1762–1767 (1989), and inhibition of gastric ulcer development with an endothelin antibody in a gastric ulcer model (Extract of Japanese Society of Experimental Gastric Ulcer, 50 (1991)) have been reported. Therefore, endothelin is assumed to be one of the mediators causing acute renal failure or cerebral vasospasm following subarachnoid hemorrhage.

Further, endothelin is secreted not only by endothelial cells but also by tracheal epithelial cells or by kidney cells (FEBS Letters, 255, 129–132 (1989), and FEBS Letters, 249, 42–46 (1989)).

Endothelin was also found to control the release of physiologically active endogenous substances such as renin, atrial natriuretic peptide, endothelium-derived relaxing factor (EDRF), thromboxane $A_2$, prostacyclin, noradrenaline, angiotensin II and substance P (Biochem. Biophys, Res. Commun., 157, 1164–1168 (1988); Biochem. Biophys, Res. Commun., 155, 20 167–172 (1989); Proc. Natl. Acad. Sci. USA, 85 1 9797–9800 (1989); J. Cardiovasc. Pharmacol., 13, S89–S92 (1989); Japan. J. Hypertension, 12, 76 (1989) and Neuroscience Letters, 102, 179–184 (1989)). Further, endothelin causes contraction of the smooth muscle of gastrointestinal tract and the uterine smooth muscle (FEBS Letters, 247, 337–340 (1989); Eur. J. Pharmacol., 154, 227–228 (1988); and Biochem. Biophys Res. Commun., 159, 317–323 (1989)). Further, endothelin was found to promote proliferation of rat vascular smooth muscle cells, suggesting a possible relevance to the arterial hypertrophy (Atherosclerosis, 78, 225–228 (1989)). Furthermore, since the endothelin receptors are present in a high density not only in the peripheral tissues but also in the central nervous system, and the cerebral administration of endothelin induces a behavioral change in animals, endothelin is likely to play an important role for controlling nervous functions (Neuroscience Letters, 97, 276–279 (1989)). Particularly, endothelin is suggested to be one of mediators for pain (Life Sciences, 49, PL61–PL65 (1991)).

Internal hyperplastic response was induced by rat carotid artery balloon endothelial denudation. Endothelin causes a significant worsening of the internal hyperplasia (J. Cardiovasc. Pharmacol., 22, 355–359 & 371–373(1993)). These data support a role of endothelin in the phathogenesis of vascular restenosis. Recently, it has been reported that both $ET_A$ and $ET_B$ receptors exist in the human prostate and endothelin produces a potent contraction of it. These results suggest the possibility that endothelin is involved in the pathophysiology of benign prostatic hyperplasia (J. Urology, 151, 763–766(1994), Molecular Pharmocol., 45, 306–311 (1994)).

On the other hand, endotoxin is one of potential candidates to promote the release of endothelin. Remarkable elevation of the endothelin levels in the blood or in the culture supernatant of endothelial cells was observed when endotoxin was exogenously administered to animals or added to the culture endothelial cells, respectively. These findings suggest that endothelin is an important mediator for endotoxin-induced diseases (Biochem. Biophys. Commun., 161, 1220–1227 (1989); and Acta Physiol. Scand., 137, 317–318 (1989)).

Further, it was reported that cyclosporin remarkably increased endothelin secretion in the renal cell culture (LLC-PKL cells) (Eur. J. Pharmacol., 180, 191–192 (1990)). Further, dosing of cyclosporin to rats reduced the glomerular filtration rate and increased the blood pressure in association with a remarkable increase in the circulating endothelin level. This cyclosporin-induced renal failure can be suppressed by the administration of endothelin antibody (Kidney Int., 37, 1487–1491 (1990)). Thus, it is assumed that endothelin is significantly involved in the pathogenesis of the cyclosporin-induced diseases.

Such various effects of endothelin are caused by the binding of endothelin to endothelin receptors widely distributed in many tissues (Am. J. Physiol., 256, R856–R866 (1989)). It is known that vasoconstriction by the endothelins is caused via at least two subtypes of endothelin receptors (J. Cardiovasc. Pharmacol., 17(Suppl.7), S119–S121 (1991)). One of the endothelin receptors is $ET_A$ receptor Selective to ET-1 rather than ET-3, and the other is $ET_B$ receptor equally active to ET-1 and ET-3. These receptor proteins are reported to be different from each other (Nature, 348, 730–735 (1990)).

These two subtypes of endothelin receptors are differently distributed in tissues. It is known that the $ET_A$ receptor is present mainly in cardiovascular tissues, whereas the $ET_B$ receptor is widely distributed in various tissues such as brain, kidney, lung, heart and vascular tissues.

Substances which specifically inhibit the binding of endothelin to the endothelin receptors are believed to antagonize various pharmacological activities of endothelin and to be useful as a drug in a wide field. Since the action of the endothelins is caused via not only the $ET_A$ receptor but also the $ET_B$ receptor, novel non-peptidic substances with ET receptor antagonistic activity to either receptor subtype are desired to block activities of the endothelins effectively in various diseases.

Endothelin is an endogenous substance which directly or indirectly (by controlling liberation of various endogenous substances) induces sustained contraction or relaxation of vascular or non-vascular smooth muscles, and its excess production or excess secretion is believed to be one of pathogeneses for hypertension, pulmonary hypertension, Raynaud's disease, bronchial asthma, gastric ulcer, diabetes, arteriosclerosis, restenosis, acute renal failure, myocardial infarction, angina pectoris, cerebral vasospasm and cerebral infarction. Further, it is suggested that endothelin serves as an important mediator involved in diseases such as restenosis, prostatauxe, endotoxin shock, endotoxin-induced multiple organ failure or disseminated intravascular coagulation, and cyclosporin-induced renal failure or hypertension.

Two endothelin receptors $ET_A$ and $ET_B$ are known so far. An antagonistic agent against the $ET_B$ receptor as well as the $ET_A$ receptor is useful as a drug. In the field of anti-endothelin agents, some non-peptidic compounds possessing antagonistic activity against endothelin receptors were already disclosed in patents (for example, EP 0526708 A1, WO 93/08799 A1). Accordingly, it is an object of the present invention to provide a novel therapeutics for the treatment of the above-mentioned various diseases by an invention of a novel and potent non-peptidic antagonist against either $ET_A$ or $ET_B$ receptor.

In order to accomplish the above object, the present inventors have developed an asymmetric conjugate addition which enables them to prepare compounds of Formula I

I

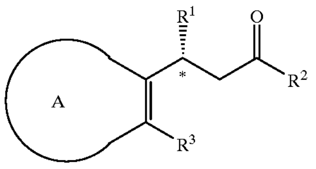

and the sterioisomer with opposite stereochemistry at C*, wherein

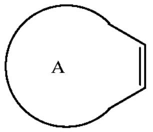

represents: 5- or 6-membered heterocyclyl, 5- or 6-membered carbocyclyl, or aryl;

$R^1$ is: aryl, $C_1$–$C_8$ alkyl, or heteroaryl;

$R^2$ is: $OR^4$, $N(R^5)_2$, H, or OH;

$R^3$ is: H, $C_1$–$C_8$ alkyl, $C_1$–$C_8$ alkoxy, halo, aryl, heteroaryl, or CHO;

$R^4$ is $C_1$–$C_8$ alkyl;

$R^5$ is H, $C_1$–$C_8$ alkyl or aryl;

and use this key intermediate to prepare endothelin antagonists, such as the compound below (Ishikawa et al. U.S. Pat. No. 5,389,620):

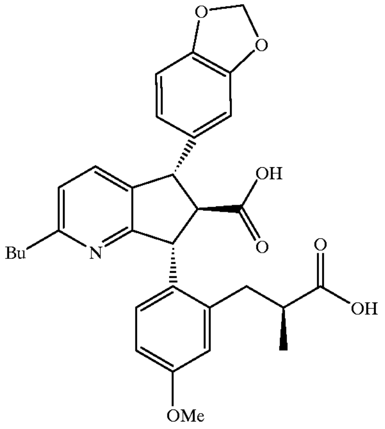

SUMMARY OF THE INVENTION

This invention relates to a key intermediate in the synthesis of an endothelin antagonist and the synthesis of this key intermediate via an asymmetric conjugate addition.

The instant invention relates to a compound of Formula I:

I

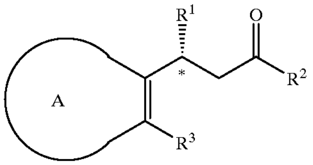

and the sterioisomer with opposite stereochemistry at C*, wherein

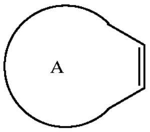

represents:

a) 5- or 6-membered heterocyclyl, wherein heterocyclyl is defined as a cyclic moiety containing one, two or three double bonds, but at least one double bond and 1, 2 or 3 heteroatoms selected from O, N and S, and the heterocyclyl is unsubstituted or substituted with one, two or three $R^{10}$ substituents, wherein R is selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, $C_3$–$C_8$ cycloalkyl, $CO(CH_2)_nCH_3$, and $CO(CH_2)_nCH_2N(R^5)_2$, b) 5- or 6-membered carbocyclyl, wherein carbocyclyl is defined as a cyclic moiety containing only carbon in the ring and containing one or two double bonds, but at least one double bond, the carbocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, $C_3$–$C_8$ cycloalkyl, $CO(CH_2)_nCH_3$, and $CO(CH_2)_nCH_2N(R^5)_2$, c) aryl, wherein aryl is as defined below, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, are unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_3$–$C_8$ cycloalkyl, $CO(CH_2)_nCH_3$, and $CO(CH_2)_nCH_2N(R^5)_2$, aryl is defined as phenyl or naphthyl, which is unsubstituted or substituted with one, two or three substituents selected from the group consisting of: OH, OBenzyl, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, $C_3$–$C_8$ cycloalkyl, $CO(CH_2)_nCH_3$, $CO(CH_2)_nCH_2N(R^5)_2$, and when two substituents are located on adjacent carbons they can join to form a 5- or 6-membered ring with one, two or three heteroatoms selected from O, N, and S, which is unsubstituted or substituted with one, two or three substituents selected from the group consisting of: H, OH, $CO_2R^6$, Br, Cl, F, I, $CF_3$, $N(R^7)_2$, $C_1$–$C_8$ alkoxy, $C_1$–$C_8$ alkyl, $C_2$–$C_8$ alkenyl, $C_2$–$C_8$ alkynyl, $C_3$–$C_8$ cycloalkyl, $CO(CH_2)_nCH_3$, and $CO(CH_2)_nCH_2N(R^5)_2$, $R^1$ is:

a) aryl, wherein aryl is as defined above, b) $C_1$–$C_8$ alkyl, or c) heteroaryl;

heteroaryl is defined as a 5- or 6-membered aromatic ring containing 1, 2 or 3 heteroatoms selected from O, N and S, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, $C_3$–$C_8$ cycloalkyl, $CO(CH_2)_nCH_3$, and $CO(CH_2)_nCH_2N(R^5)_2$, $R^2$ is:

a) $OR^4$, b) $N(R^5)_2$, c) H, or d) OH;

$R^3$ is:

a) H, b) $C_1$–$C_8$ alkyl, c) $C_1$–$C_8$ alkoxy, d) Br, Cl, F, I, e) aryl, f) heteroaryl, g) $C(OR^a)(OR^b)$, wherein $R^a$ and $R^b$ are independently $(C_1$–$C_5)$alkyl and may be connected to form a 5- or 6-membered heterocyclic ring containing two oxygens, or h) CHO;

n is: 0 to 5;

$R^4$ is $C_1$–$C_8$ alkyl;

$R^5$ is H, $C_1$–$C_8$ alkyl, or aryl;

$R^6$ is H, $C_1$–$C_8$ alkyl, and aryl; and $R^7$ is H, $C_1$–$C_8$ alkyl, or aryl, when there are two $R^7$ substituents on a nitrogen they can join to form a 3- through 6-membered ring, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, $C_3$–$C_8$ cycloalkyl, $CO(CH_2)_nCH_3$, and $CO(CH_2)_nCH_2N(R^5)_2$.

DETAILED DESCRIPTION OF THE INVENTION

The instant invention relates to a compound of Formula I:

I

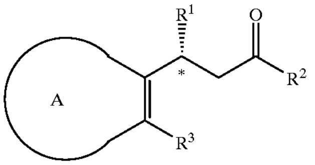

and the sterioisomer with opposite stereochemistry at the starred carbon (hereinafter referred to as C* and the carbon being identified in the structures with an asterix), wherein

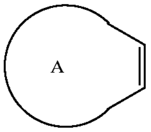

represents:

a) 5- or 6-membered heterocyclyl, wherein heterocyclyl is defined as a cyclic moiety containing one, two or three double bonds, but at least one double bond and 1, 2 or 3 heteroatoms selected from O, N and S, and the heterocyclyl is unsubstituted or substituted with one, two or three $R^{10}$ substituents, where in $R^{10}$ is selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, $C_3$–$C_8$ cycloalkyl, $CO(CH_2)_nCH_3$, and $CO(CH_2)_nCH_2N(R^5)_2$, b) 5- or 6-membered carbocyclyl, wherein carbocyclyl is defined as a cyclic moiety containing only carbon in the ring and containing one or two double bonds, but at least one double bond, the carbocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, $C_3$–$C_8$ cycloalkyl, $CO(CH_2)_nCH_3$, and $CO(CH_2)_nCH_2N(R^5)_2$, c) aryl, wherein aryl is as defined below, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, are unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_3$–$C_8$ cycloalkyl, $CO(CH_2)_nCH_3$, and $CO(CH_2)_nCH_2N(R^5)_2$, aryl is defined as phenyl or naphthyl, which is unsubstituted or substituted with one, two or three substituents selected from the group consisting of: OH, OBenzyl, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, $C_3$–$C_8$ cycloalkyl, $CO(CH_2)_nCH_3$, $CO(CH_2)_nCH_2N(R^5)_2$, and when two substituents are located on adjacent carbons they can join to form a 5- or 6-membered ring with one, two or three heteroatoms selected from O, N, and S, which is unsubstituted or substituted with one, two or three substituents selected from the group consisting of: H, OH, $CO_2R^6$, Br, Cl, F, I, $CF_3$, $N(R^7)_2$, $C_1$–$C_8$ alkoxy, $C_1$–$C_8$ alkyl, $C_2$–$C_8$ alkenyl, $C_2$–$C_8$ alkynyl, $C_3$–$C_8$ cycloalkyl, $CO(CH_2)_nCH_3$, and $CO(CH_2)_nCH_2N(R^5)_2$, $R^1$ is:

a) aryl, wherein aryl is as defined above, b) $C_1$–$C_8$ alkyl, or c) heteroaryl;

heteroaryl is defined as a 5- or 6-membered aromatic ring containing 1, 2 or 3 heteroatoms selected from O, N and S, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, $C_3$–$C_8$ cycloalkyl, $CO(CH_2)_nCH_3$, and $CO(CH_2)_nCH_2N(R^5)_2$, $R^2$ is:

a) $OR^4$, b) $N(R^5)_2$, c) H, or d) OH;

$R^3$ is:

a) H, b) $C_1$–$C_8$ alkyl, c) $C_1$–$C_8$ alkoxy, d) Br, Cl, F, I, e) aryl, f) heteroaryl, g) $C(OR^a)(OR^b)$, wherein $R^a$ and $R^b$ are independently ($C_1$–$C_5$)alkyl and may be connected to form a 5- or 6-membered heterocyclic ring containing two oxygens, or h) CHO;

n is: 0 to 5;

$R^4$ is $C_1$–$C_8$ alkyl;

$R^5$ is H, $C_1$–$C_8$ alkyl, or aryl;

$R^6$ is H, $C_1$–$C_8$ alkyl, and aryl; and $R^7$ is H, $C_1$–$C_8$ alkyl, or aryl, when there are two $R^7$ substituents on a nitrogen they can join to form a 3- through 6-membered ring, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, $C_3$–$C_8$ cycloalkyl, $CO(CH_2)_nCH_3$, and $CO(CH_2)_nCH_2N(R^5)_2$.

An embodiment of the invention includes a compound of Formula II:

II

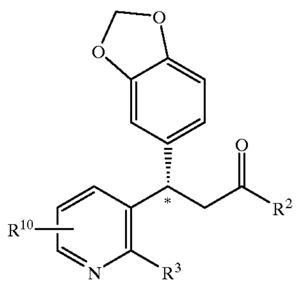

and the sterioisomer with opposite stereochemistry at C*, wherein $R^2$ is:

a) $OR^4$, b) $N(R^5)_2$, c) H, or d) OH;

$R^3$ is:

a) H, b) $C_1$–$C_8$ alkyl, c) $C_1$–$C_8$ alkoxy, d) Br, Cl, F, I, e) aryl, f) heteroaryl, g) $C(OR^a)(OR^b)$, wherein $R^a$ and $R^b$ are independently ($C_1$–$C_5$)alkyl and may be connected to form a 5- or 6-membered heterocyclic ring containing two oxygens, or h) CHO;

$R^4$ is $C_1$–$C_8$ alkyl;

$R^5$ is H, $C_1$–$C_8$ alkyl or aryl; and $R^{10}$ is:

a) OH, b) $CO_2R^4$, c) halo, wherein halo is Br, Cl, F, or I, d) $CF_3$, e) $N(R^5)_2$, f) $C_1$–$C_8$ alkoxy, g) $C_1$–$C_8$ alkyl, h) $C_2$–$C_8$ alkenyl, i) $C_2$–$C_8$ alkynyl, j) $C_3$–$C_8$ cycloalkyl, k) $CO(CH_2)_nCH_3$, or l) $CO(CH_2)_nCH_2N(R^5)_2$.

An embodiment of the invention includes a compound of Formula III:

III

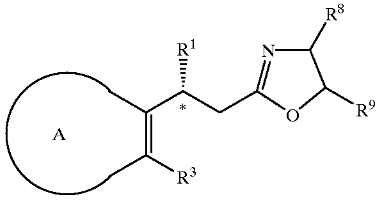

and the sterioisomer with opposite stereochemistry at C*, wherein

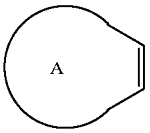

represents:

a) 5- or 6-membered heterocyclyl, wherein heterocyclyl is defined as a cyclic moiety containing one, two or three double bonds, but at least one double bond and 1, 2 or 3 heteroatoms selected from O, N and S, and the heterocyclyl is unsubstituted or substituted with one, two or three $R^{10}$ substituents, wherein R is selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, $C_3$–$C_8$ cycloalkyl, $CO(CH_2)_nCH_3$, and $CO(CH_2)_nCH_2N(R^5)_2$, b) 5- or 6-membered carbocyclyl, wherein carbocyclyl is defined as a cyclic moiety containing only carbon in the ring and containing one or two double bonds, but at least one double bond, the carbocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, $C_3$–$C_8$ cycloalkyl, $CO(CH_2)_nCH_3$, and $CO(CH_2)_nCH_2N(R^5)_2$, c) aryl, wherein aryl is as defined below, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, are unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_3$–$C_8$ cycloalkyl, $CO(CH_2)_nCH_3$, and $CO(CH_2)_nCH_2N(R^5)_2$, aryl is defined as phenyl or naphthyl, which is unsubstituted or substituted with one, two or three substituents selected from the group consisting of: OH, OBenzyl, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, $C_3$–$C_8$ cycloalkyl, $CO(CH_2)_nCH_3$, $CO(CH_2)_nCH_2N(R^5)_2$, and when two substituents are located on adjacent carbons they can join to form a 5- or 6-membered ring with one, two or three heteroatoms selected from O, N, and S, which is unsubstituted or substituted with one, two or three substituents selected from the group consisting of: H, OH, $CO_2R^6$, Br, Cl, F, I, $CF_3$, $N(R^7)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, $R^1$ is:

a) aryl, wherein aryl is as defined above, b) $C_1$–$C_8$ alkyl, or c) heteroaryl;

heteroaryl is defined as a 5- or 6-membered aromatic ring containing 1, 2 or 3 heteroatoms selected from O, N and S, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, $C_3$–$C_8$ cycloalkyl, $CO(CH_2)_nCH_3$, and $CO(CH_2)_nCH_2N(R^5)_2$, $R^3$ is:

a) H, b) $C_1$–$C_8$ alkyl, c) $C_1$–$C_8$ alkoxy, d) Br, Cl, F, I, e) aryl, f) heteroaryl, g) $C(OR^a)(OR^b)$, wherein $R^a$ and $R^b$ are independently $(C_1$–$C_5)$alkyl and may be connected to form a 5- or 6-membered heterocyclic ring containing two oxygens, or h) CHO;

n is: 0 to 5;

$R^4$ is $C_1$–$C_8$ alkyl;

$R^5$ is H, $C_1$–$C_8$ alkyl, or aryl;

$R^6$ is H, $C_1$–$C_8$ alkyl,or aryl;

$R^7$ is H, $C_1$–$C_8$ alkyl, or aryl, when there are two $R^7$ substituents on a nitrogen they can join to form a 3- through 6-membered ring, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, $C_3$–$C_8$ cycloalkyl, $CO(CH_2)_nCH_3$, and $CO(CH_2)_nCH_2N(R^5)_2$, $R^8$ and $R^9$ are independently:

a) aryl, wherein aryl is as defined in A(c) above, b) heteroaryl, wherein heteroaryl is as defined in $R^1$(b) above, c) $CH_2OR^4$, d) aryl-$SCH_3$, wherein aryl is as defined in A(c) above, e) $C_1$–$C_8$ alkyl, or f) H, so long as both $R^8$ and $R^9$ are not both H at the same time.

Another embodiment of the invention is a compound of Formula IV:

IV

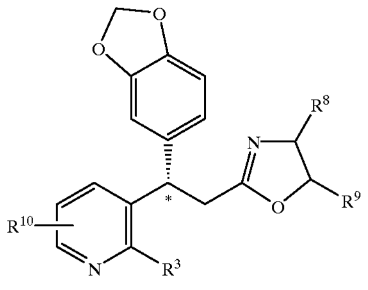

and the sterioisomer with opposite stereochemistry at C*, wherein $R^3$ is:

a) H, b) $C_1$–$C_8$ alkyl, c) $C_1$–$C_8$ alkoxy, d) Br, Cl, F, I, e) aryl, f) heteroaryl, g) $C(OR^a)(OR^b)$, wherein $R^a$ and $R^b$ are independently $(C_1$–$C_5)$alkyl and may be connected to form a 5- or 6-membered heterocyclic ring containing two oxygens, or h) CHO;

$R^4$ is $C_1$–$C_8$ alkyl;

$R^5$ is H, $C_1$–$C_8$ alkyl or aryl;

$R^8$ and $R^9$ are independently:

a) aryl, wherein aryl is as defined in A(c) above, b) heteroaryl, wherein heteroaryl is as defined in $R^1$(b) above, c) $CH_2OR^4$, d) aryl-$SCH_3$, wherein aryl is as defined in A(c) above, e) $C_1$–$C_8$ alkyl, or f) H, so long as both $R^8$ and $R^9$ are not both H at the same time; and $R^{10}$ is:

a) OH, b) $CO_2R^4$, c) halo , wherein halo is Br, Cl, F, or I, d) $CF_3$, e) $N(R^5)_2$, f) $C_1$–$C_8$ alkoxy, g) $C_2$–$C_8$ alkyl, h) $C_2$–$C_8$ alkenyl, i) $C_2$–$C_8$ alkynyl, j) $C_3$–$C_8$ cycloalkyl, k) $CO(CH_2)_nCH_3$, or l) $CO(CH_2)_nCH_2N(R^5)_2$.

A further embodiment of the invention is a compound of Formula V

V

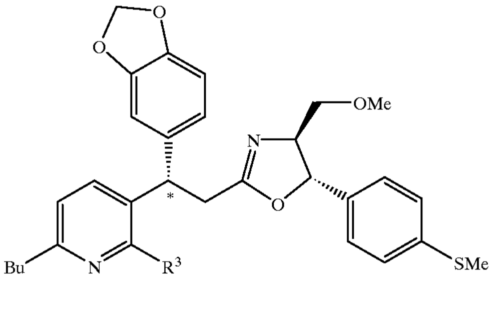

or its enantiomer, wherein $R^3$ is I, Br, Cl, F, CHO or $C(OR^a)(OR^b)$, wherein $R^a$ and $R^b$ are independently $(C_1$–$C_5)$alkyl and may be connected to form a 5- or 6-membered heterocyclic ring containing two oxygens.

An embodiment of the invention is a process for the preparation of a compound of Formula I:

I

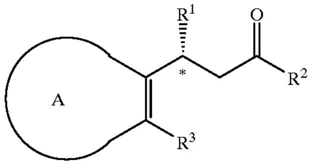

and the sterioisomer with opposite stereochemistry at C*, wherein

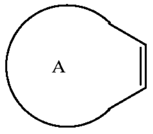 represents:

a) 5- or 6-membered heterocyclyl, wherein heterocyclyl is defined as a cyclic moiety containing one, two or three double bonds, but at least one double bond and 1, 2 or 3 heteroatoms selected from O, N and S, and the heterocyclyl is unsubstituted or substituted with one, two or three $R^{10}$ substituents, wherein $R^{10}$ is selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, $C_3$–$C_8$ cycloalkyl, $CO(CH_2)_nCH_3$, and $CO(CH_2)_nCH_2N(R^5)_2$, b) 5- or 6-membered carbocyclyl, wherein carbocyclyl is defined as a cyclic moiety containing only carbon in the ring and containing one or two double bonds, but at least one double bond, the carbocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, $C_3$–$C_8$ cycloalkyl, $CO(CH_2)_nCH_3$, and $CO(CH_2)_nCH_2N(R^5)_2$, c) aryl, wherein aryl is as defined below, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, are unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_3$–$C_8$ cycloalkyl, $CO(CH_2)_nCH_3$, and $CO(CH_2)_nCH_2N(R^5)_2$, aryl is defined as phenyl or naphthyl, which is unsubstituted or substituted with one, two or three substituents selected from the group consisting of: OH, OBenzyl, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, $C_3$–$C_8$ cycloalkyl, $CO(CH_2)_nCH_3$, and $CO(CH_2)_nCH_2N(R^5)_2$, and when two substituents are located on adjacent carbons they can join to form a 5- or 6-membered ring with one, two or three heteroatoms selected from O, N, and S, which is unsubstituted or substituted with one, two or three substituents selected from the group consisting of: H, OH, $CO_2R^6$, Br, Cl, F, I, $CF_3$, $N(R^7)_2$, $C_1$–$C_8$ alkoxy, $C_1$–$C_8$ alkyl, $C_2$–$C_8$ alkenyl, $C_2$–$C_8$ alkynyl, $C_3$–$C_8$ cycloalkyl, $CO(CH_2)_nCH_3$, and $CO(CH_2)_nCH_2N(R^5)_2$, $R^1$ is:

a) aryl, wherein aryl is as defined above, b) $C_1$–$C_8$ alkyl, or c) heteroaryl, heteroaryl is defined as a 5- or 6-membered aromatic ring containing 1, 2 or 3 heteroatoms selected from O, N and S, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, $C_3$–$C_8$ cycloalkyl, $CO(CH_2)_nCH_3$, and $CO(CH_2)_nCH_2N(R^5)_2$;

$R^2$ is:

a) $OR^4$, b) $N(R^5)_2$, c) H, or d) OH;

$R^3$ is:

a) H, b) $C_1$–$C_8$ alkyl, c) $C_1$–$C_8$ alkoxy, d) Br, Cl, F, I, e) aryl, f) heteroaryl, or g) $C(OR^a)(OR^b)$, wherein $R^a$ and $R^b$ are independently $(C_1$–$C_5)$alkyl and may be connected to form a 5- or 6-membered heterocyclic ring containing two oxygens;

n is: 0 to 5;

$R^4$ is $C_1$–$C_8$ alkyl;

$R^5$ is H, $C_1$–$C_8$ alkyl or aryl;

$R^6$ is H, $C_1$–$C_8$ alkyl, or aryl; and $R^7$ is H, $C_1$–$C_8$ alkyl, or aryl, when there are two $R^7$ substituents on a nitrogen they can join to form a 3- through 6-membered ring, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, $C_3$–$C_8$ cycloalkyl, $CO(CH_2)_nCH_3$, and $CO(CH_2)_nCH_2N(R^5)_2$;

comprising the steps of:

(1) reacting a vinyl-substituted, chiral oxazoline of Formula VI,

VI

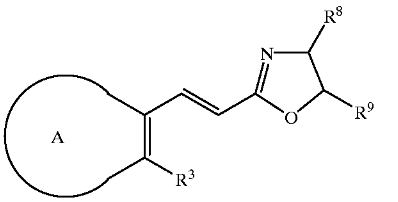

wherein $R^8$ and $R^9$ are independently:

a) aryl, wherein aryl is as defined in A(c) above, b) heteroaryl, wherein heteroaryl is as defined in $R^1$(b) above, c) $CH_2OR^4$, d) aryl-$SCH_3$, wherein aryl is as defined in A(c) above, e) $C_1$–$C_8$ alkyl, or f) H, so long as both $R^8$ and $R^9$ are not both H at the same time;

with an amount of an organolithium compound, $R^1Li$, in an aprotic solvent at a temperature between about −100° to about 25° C. to produce a chiral adduct; and (2) hydrolyzing the chiral adduct with a hydrolyzing reagent to produce a compound of Formula I.

The process conditions for the process recited above, wherein the amount of $R^1Li$ added is between about 1 to about 4 equivalents, preferably about 2 to about 3 equivalents.

The process as recited above, wherein the suitable aprotic solvents include tetrahydrofuran, diethyl ether, MTBE (methyl t-butyl ether), benzene, toluene, pentane, hexane, dioxane and a mixture of said solvents, in addition to aprotic solvents that would be readily apparent to a person skilled in the art; and the temperature range is about −100° C. to about 25° C., and preferably about −78° C. to about 0°C.

A preferred embodiment of the invention is wherein the amount of $R^1Li$ added is between about 2 to about 3 equivalents, the aprotic solvent is tetrahydrofuran and the temperature range is between about −78° C. to about 0°°C.

The process recited above, wherein the hydrolysis step is accomplished via heating with a hydrolyzing reagent such as protic acid in an alcohol solvent, which is further defined as $H_2SO_4$ and isopropyl alcohol. Suitable protic acids include $H_2SO_4$, $H_2NO_3$, HCl, acetic acid, trifluoroacetic acid, and other acids that would be readily apparent to those skilled in the art. Suitable alcohol solvents are $C_1$–$C_8$ straight-chain and branched alkyl alcohols, examples are methanol, ethanol, propanol, isopropanol, and butanol.

Alternatively, the hydrolysis step can be performed by treatment with other hydrolyzing reagents including, but not limited to, suitable electrophilic reagents, such as Lewis acids or alkylating agents. Suitable Lewis acids include $TiCl_4$, $BF_3$, $BCl_3$, $SnCl_4$, $AlCl_3$, and $TiCl_2(OiPr)_2$. Suitable alkylating agents include alkyl iodides, alkyl triflates, and anhydrides, examples of these electrophilic reagents include methyl iodide, methyl triflate, ethyl iodide, ethyl triflate and triflic anhydride.

Yet another embodiment of the invention is the process recited above for the preparation of a compound of Formula II:

II

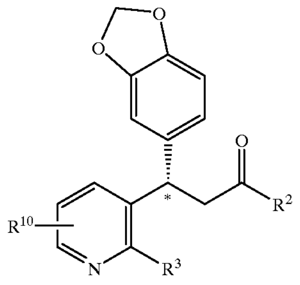

and the sterioisomer with opposite stereochemistry at C*, wherein $R^2$, $R^3$, $R^4$, $R^5$ and n are as defined above; and $R^{10}$ is:

a) OH, b) $CO_2R^4$, c) halo, wherein halo is Br, Cl, F, or I, d) $CF_3$, e) $N(R^5)_2$, f) $C_1$–$C_8$ alkoxy, g) $C_1$–$C_8$ alkyl, h) $C_2$–$C_8$ alkenyl, i) $C_2$–$C_8$ alkynyl, j) $C_3$–$C_8$ cycloalkyl, k) $CO(CH_2)_nCH_3$, or l) $CO(CH_2)_nCH_2N(R^5)_2$;

comprising the steps of:

(1) reacting a vinyl-substituted, chiral oxazoline of Formula VII

VII

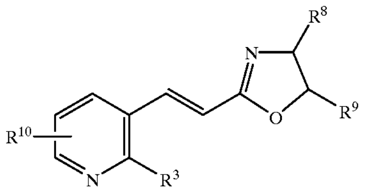

wherein $R^8$ and $R^9$ are as defined above;

with an amount of an organolithium compound of Formula VIII:

VIII

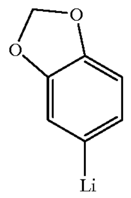

in an aprotic solvent at a temperature between about −78° and 0° C. to produce a chiral adduct; and (2) hydrolyzing the chiral adduct with a hydrolyzing reagent to produce a compound of Formula II.

A subembodiment of the invention is the process as recited above wherein the amount of the organolithium compound of Formula VIII used in step 1 is between about 2 to about 3 equivalents relative to the chiral oxazoline.

Another subembodiment is the process as recited above wherein the aprotic solvent used in step 1 is chosen from a group consisting of tetrahydrofuran, diethyl ether, MTBE (methyl t-butyl ether), benzene, toluene, pentane, hexane, dioxane and a mixture of said solvents.

Yet another subembodiment of the invention is the process as recited above wherein the hydrolyzing reagent used in step 2 is $H_2SO_4$.

Another embodiment of the invention is the process for the preparation of a compound of Formula IV

IV

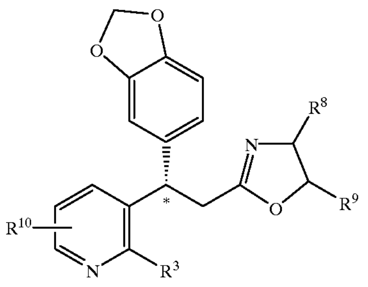

and the sterioisomer with opposite stereochemistry at C*, wherein $R^3$, $R^4$, $R^5$, $R^8$, $R^9$, $R^{10}$, and n are as defined above which comprises reacting a vinyl-substituted, chiral oxazoline of Formula VII

VII

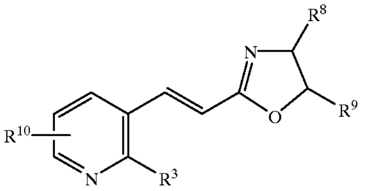

with at least 2 equivalents of an organolithium compound of Formula VIII

VIII

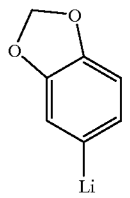

in an aprotic solvent at a temperature between about −78° and 0° C.

The process as recited above, for the preparation of the compound of Formula IX:

IX

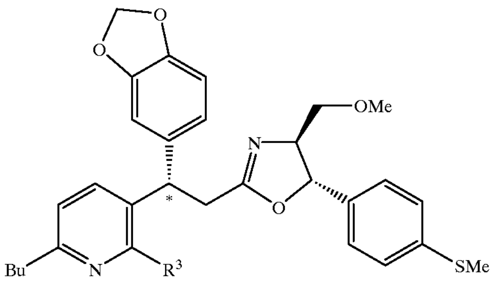

or its enantiomer, wherein $R^3$ is I, Br, Cl, F or $C(OR^a)(OR^b)$, wherein $R^a$ and $R^b$ are independently $(C_1$–$C_5)$alkyl and may be connected to form a 5- or 6-membered heterocyclic ring containing two oxygens, which comprises reacting a vinyl-substituted, chiral oxazoline of Formula X

X

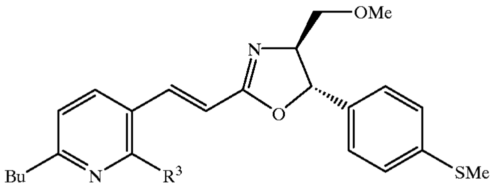

with at least 2 equivalents of an organolithium compound of Formula VIII

VIII

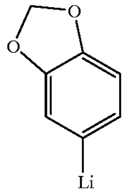

in an aprotic solvent at a temperature between about −78° and 0° C.

It is further understood that the substituents recited above would include the definitions recited below.

The alkyl-substituents recited above denote straight and branched chain hydrocarbons of the length specified such as methyl, ethyl, isopropyl, isobutyl, tert-butyl, neopentyl, isopentyl, etc.

The alkenyl-substituents denote alkyl groups as described above which are modified so that each contains a carbon to carbon double bond such as vinyl, allyl and 2-butenyl.

The alkynyl-substituents denote alkyl groups as described above which are modified so that each contains a carbon to carbon triple bond such as ethynyl,and propynyl.

Cycloalkyl denotes rings composed of 3 to 8 methylene groups, each of which may be substituted or unsubstituted with other hydrocarbon substituents, and include for example cyclopropyl, cyclopentyl, cyclohexyl and 4-methylcyclohexyl.

of: OH, $CO_2R^4$, Br, Cl, F, I, $CF_3$, $N(R^5)_2$, $C_1$–$C_8$ alkoxy, $C_3$–$C_8$ cycloalkyl, $CO(CH_2)_nCH_3$, and $CO(CH_2)_nCH_2N(R^5)_2$.

The heteroaryl substituent represents an carbazolyl, furanyl, thienyl, pyrrolyl, isothiazolyl, imidazolyl, isoxazolyl, thiazolyl, oxazolyl, pyrazolyl, pyrazinyl, pyridyl, pyrimidyl, purinyl. The heterocyclyl substituent represents a pyridyl, pyrimidyl, thienyl, furanyl, oxazolidinyl, oxazolyl, thiazolyl, isothiazolyl, pyrazolyl, triazolyl, imidazolyl, imidazoldinyl, thiazolidilnyl, isoxazolyl, oxadiazolyl, thiadiazolyl, morpholinyl, piperidinyl, piperazinyl, pyrrolyl, or pyrrolidinyl.

The vinyl-substituted, chiral oxazolines of Formula VI

VI

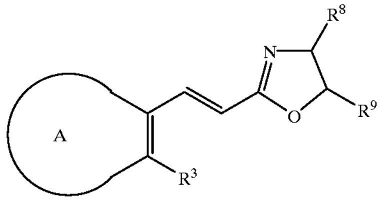

can generally be prepared by the following protocol. Scheme 1 below outlines the synthesis of the chiral auxiliary.

SCHEME 1

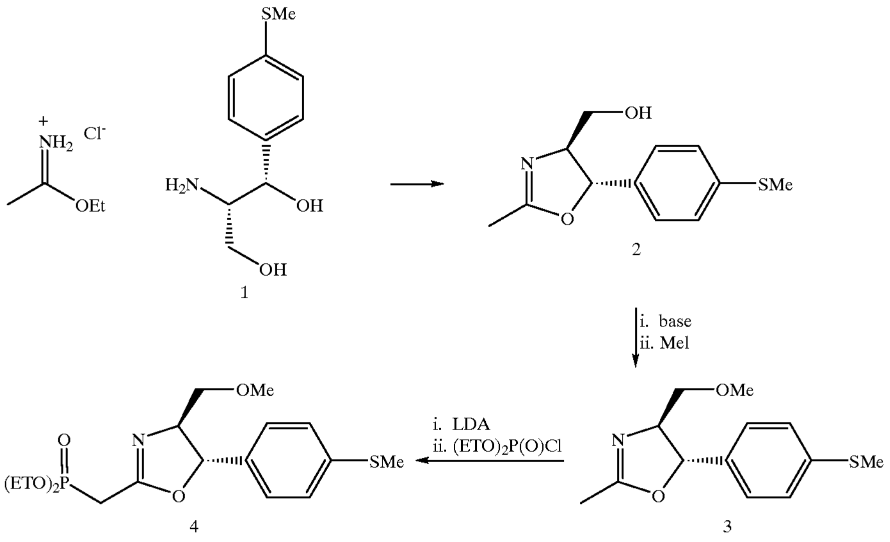

The alkoxy substituent represents an alkyl group as described above attached through an oxygen bridge.

Additionally, it is understood that the terms alkyl, alkenyl, akynyl, cycloalkyl and alkoxy can be substituted with one, two or three substituents selected from the group consisting Scheme 2 describes the addition of the chiral auxiliary 4 to form a vinyl-substituted, chiral oxazolines of Formula II. Unsaturated oxazoline 6 was prepared via the Homer-Emmons reaction of phosphonate 4 with bromopyridine aldehyde 5.

SCHEME 2

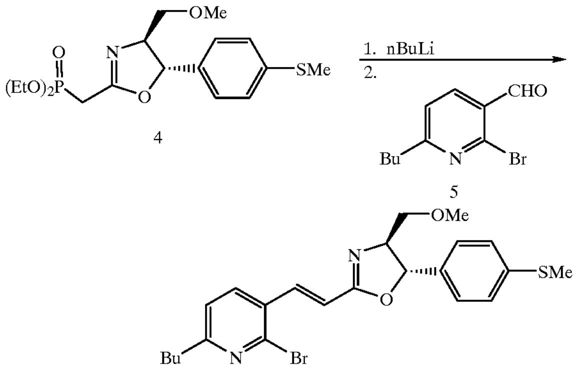

4 5 6

Conjugate addition of the lithium anion of 4-bromo-1,2-(methylenedioxy)benzene 7 to 6 produced the desired

SCHEME 3

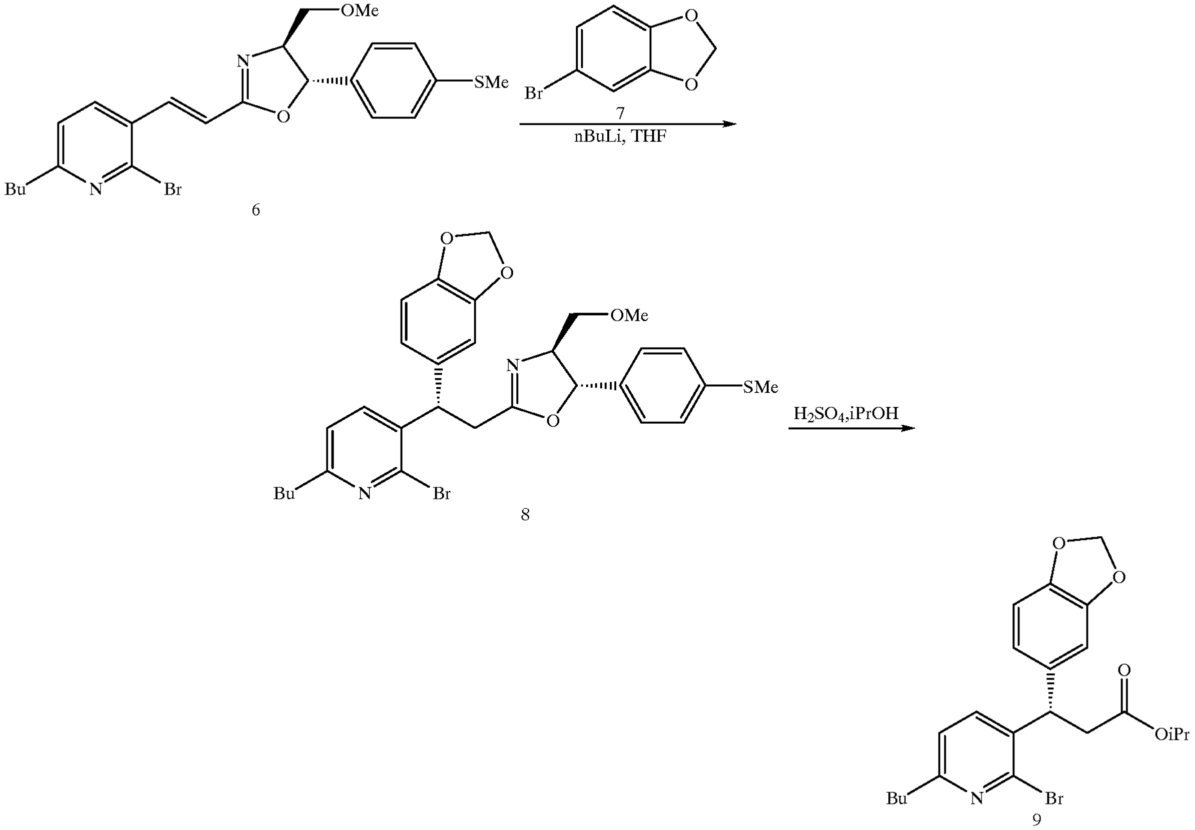

6 7 8 9 adduct 8 in high diastereomeric excess. (Scheme 3) Hydrolysis of oxazoline 8 was accomplished by refluxing in isopropyl alcohol with concentrated sulfuric acid to yield the isopropyl ester 9, which is an example of a compound of Formula 1. Alternatively, the halide in compound 6 may be transformed into the corresponding carbonyl by methods well known in the literature and then protected as an acetal or another aldehyde equivalent. See, for example, Theodora W. Greene and Peter G. M. Wuts, *Protective Groups in Organic Synthesis*, John Wiley & Sons (1991).

As previously mentioned, the compounds of Formula 1, such as compound 9, are useful intermediates in the syntheses of endothelin antagonists. Scheme 4 below outlines a synthesis of an endothelin antagonist using compound 9.

SCHEME 4
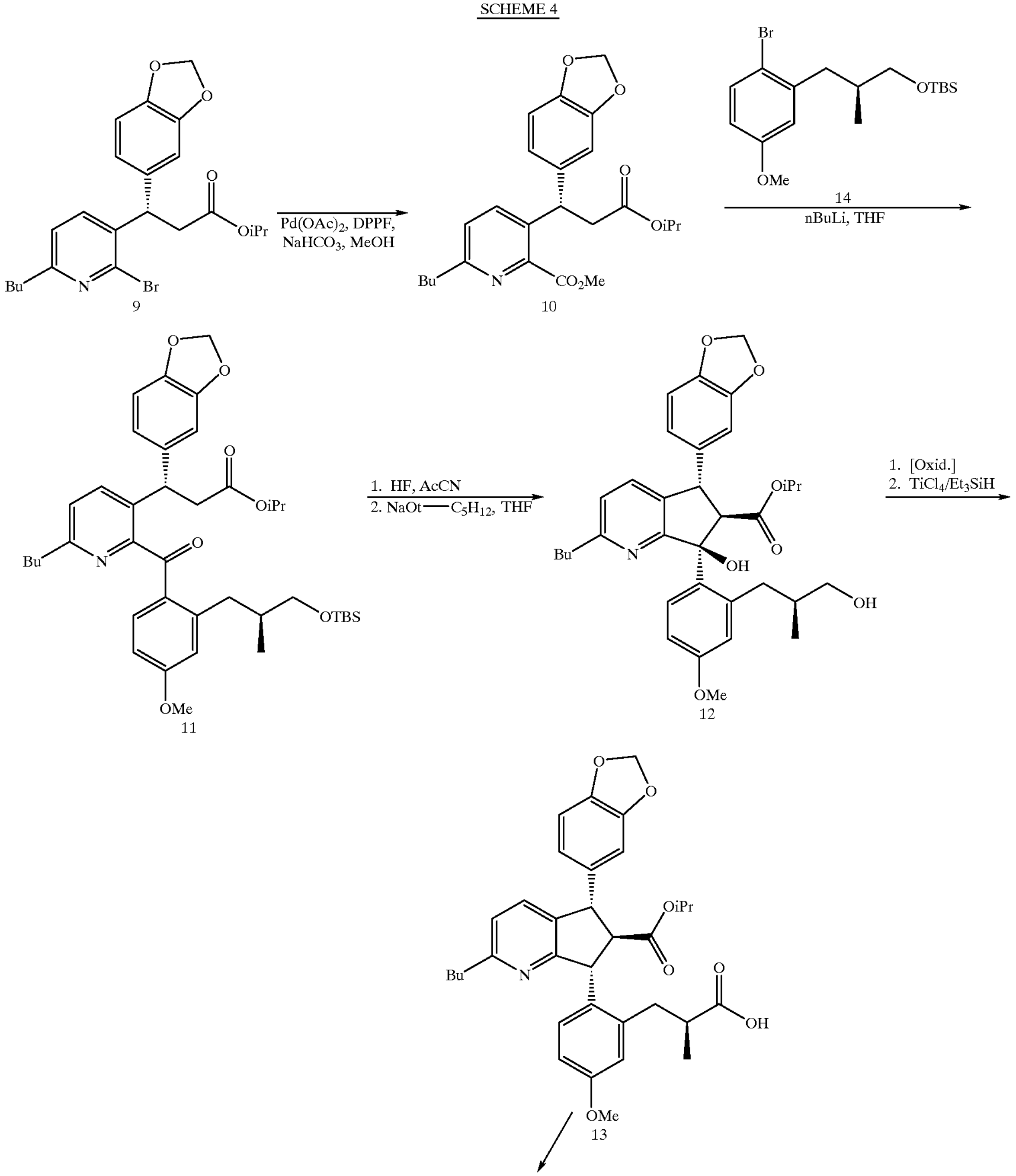

-continued

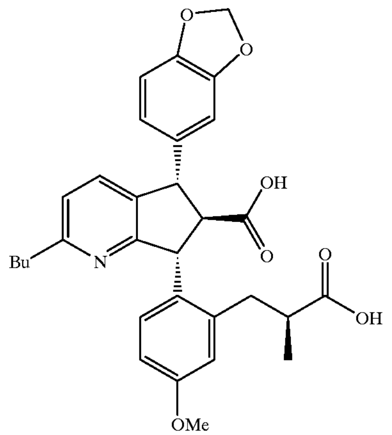

15

Carbonylation of the isopropyl ester 9 using catalytic palladium in methanol produced diester 10. Inverse addition of the lithium anion of 14 to methyl ester 10 at −78° C. generated the desired ketoester11. Compound 11 was then treated with aqueous HF to remove the silyl protecting group. The deprotected ketoester was then cyclized with sodium t-amylate to form aldol 12. Oxidation of 12 may then be accomplished using reagents well known in the art, such as Jone's reagent ($CrO_3/H_2SO_4$), to afford the carboxylic acid. Finally, the carboxylic acid analog of 12 can be deoxygenated by the action of $TiCl_4$ and triethylsilane, for example, to produce 13. De-esterification then produces the target endothelin antagonist 15.

The instant invention can be understood further by the following examples, which do not constitute a limitation of the invention. All NMR data presented below are of samples dissolved in $CDCl_3$ unless otherwise noted.

EXAMPLE 1

16

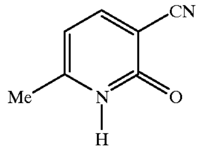

Preparation of 16

Compound 16 is a commericially available starting material, for example, see Aldrich Chemical Company, Milwaukee, Wis., USA 53201.

EXAMPLE 2

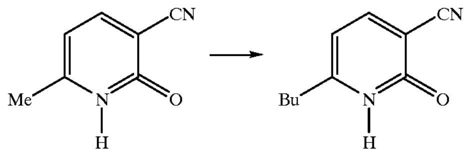

16 17

Preparation of 17

Diisopropyl amine (MW 101.19, d 0.772, 2.1 equ, 20.54 mL) in 200 mL THF. Cool to −50° C. and add n-BuLi (1.6 M in hexanes, 2.05 equ, 96 mL), allowing solution to warm to −20° C. Age 0–3° C. for 15 min, then cool to −30° C. and add 16 (MW 134.14, 75 mmol, 10.0 g). Age 0° C. to 43° C. for 2 h. Cool to −50° C. and add bromopropane (MW 123.00, d 1.354, 1.0 equ, 6.8 mL). Warm to 25° C. over 30 min, and age 30 min. Add $NH_4Cl$ and $CH_2Cl_2$. Dry organic (magnesium sulfate) then evaporate in vacuo to afford 61% of 17.

EXAMPLE 3

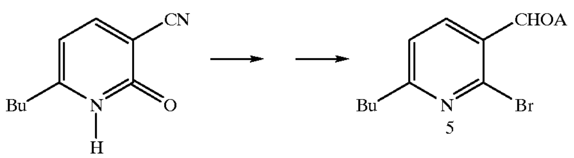

17 5

Preparation of 5

Mix 17 (MW 176.22, 46 mmol) and PBr3 (MW 270.70, d 2.880, 2.5 equ, 10.8 mL) and age at 160° C. After 2 h, cool to 25° C. and add some $CH_2Cl_2$. Slowly quench by adding water. Separate layers and wash aqueous two times with $CH_2Cl_2$. Combine organic layers and dry (magnesium sulfate). Concentrate and isolate solid by silica gel chromatography (90:10 hexanes:ethyl acetate) in 60% yield (MW 239.12, 6.60 g). Dissolve product of bromination reaction (MW 239.12, 27.6 mmol, 6.60 g) in 66 mL toluene and cool to −42° C. Slowly add DIBAL (1.5 M in toluene, 2 equ, 37 mL) and age 1 h at −42° C. Add HCl (2 N, 10 equ, 134 mL) and stir vigorously for 30 min. Dilute with ethyl acetate, separate layers, and wash aqueous with ethyl acetate. Combine organic layers, dry (magnesium sulfate), and concentrate in vacuo to afford 90% (MW 242.11, 6.01 g) of 5.

EXAMPLE 4

18A

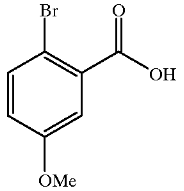

Preparation of 18A

Compound 18A is a commericially available starting material, for example, see Lancaster Synthesis, P.O. Box 1000, Windham, N.H. 03087-9977 or Ryan Scientific, Inc., P.O. Box 845, Isle of Palms, S.C. 29451-0845.

EXAMPLE 5

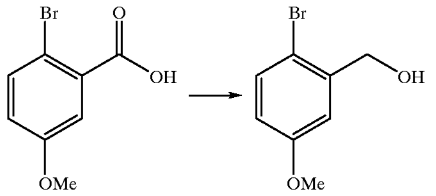

18A 18

Preparation of 18

18A (MW 231.05, 130 mmol, 30.0 g) in 300 mL $CH_2Cl_2$ at 0° C. Add $BH_3$-$SMe_2$ (3 equ, 25.2 mL) and age for 2 h at 25° C. Quench into aqueous 2 N HCl and separate layers. Dry organic (magnesium sulfate) and concentrate in vacuo to obtain 94% yield of 18 (MW 217.06, 25.5 g).

EXAMPLE 6

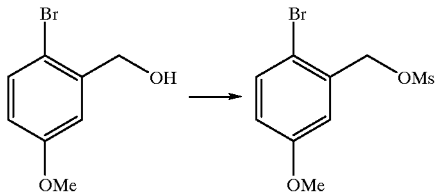

18 19

Preparation of 19

Dissolve 18 (MW 217.06, 47.2 mmol, 10.24 g) in 55 mL $CH_2Cl_2$ and cool to −20° C. Add diispropylethylamine, DIEA, (MW 129.25, d 0.742, 1.3 equ, 10.69 mL) then methane sulfonyl chloride (MsCl) (MW 114.55, d 1.480, 1.2 equ, 4.38 mL). Age −5° C. to 0° C. for 1 h then quench into 55 mL water. Extract with $CH_2Cl_2$ then wash with 1N $H_2SO_4$ (40 mL), then brine. Dry organic layers (magnesium sulfate) and concentrate in vacuo to afford 19 (MW 295.15, 13.23 g) in 95% yield.

EXAMPLE 8

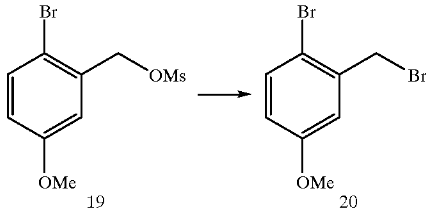

19 20

Preparation of 20

19 (MW 295.15, 44.8 mmol, 13.23 g) in 44 mL dimethylacetamide (DMAC). Add NaBr (MW 102.90, 2 equ, 9.22 g) and age 1 h. Add 88 mL water and collect solid by filtration. Wash cake with water and dry by suction. Quantitative yield of 20 (MW 279.96, 12.54 g) is obtained.

EXAMPLE 9

21

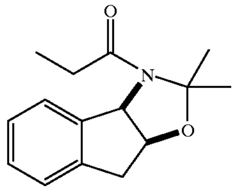

Preparation of 21

21A

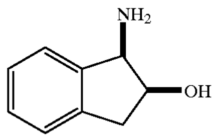

Step A: Preparation of 21A

Compound 21A is a commercially available starting material, for example, see DSM Andeno, Grubbenvorsterweg 8, P.O. Box 81, 5900 AB Venlo,The Netherlands.

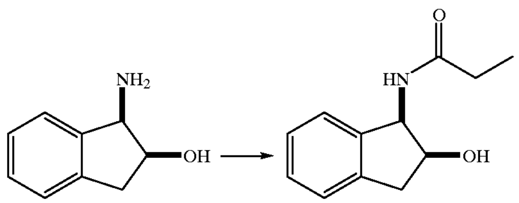

21A 21B

Step B: Preparation of 21B $Na_2CO_3$ (MW 105.99, 1.5 equ, 8.8 g) dissolved in 82 mL water. Add a solution of (1R,2S) aminoindanol 21A (MW 149.19, 55.0 mmol, 8.2 g) in 160 mL $CH_2Cl_2$. Cool to −5° C. and add propionyl chloride (MW 92.53, d 1.065, 1.3 equ, 6.2 mL). Warm to 25° C. and age 1 h. Separate layers and dry organic (magnesium sulfate). Concentrate in vacuo to afford 21B (MW 205.26, 10 g) in 89% isolated yield.

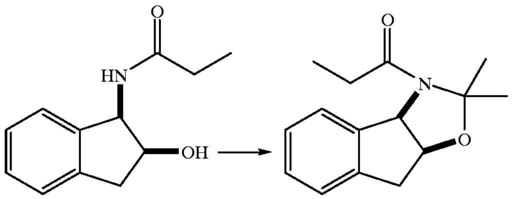

21B 21

Step C: Preparation of 21

To a solution of 21B (MW 205.26, 49.3 mmol, 10 g) in 200 mL THF, add pyridinium p-toluenesulfonate (PPTS) (MW 251.31, 0.16 equ, 2 g) then methoxypropene (MW 72.11, d 0.753, 2.2 equ, 10.4 mL). Age 2 h at 38° C., then add aqueous sodium bicarbonate and ethyl acetate. The organic layer was dried (magnesium sulfate). After concentration in vacuo, 21 (MW 245.32, 12.09 g) was formed in quantitative yield.

EXAMPLE 10

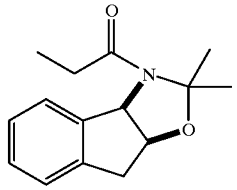

21

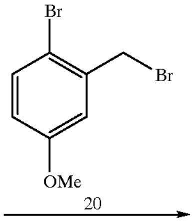

20

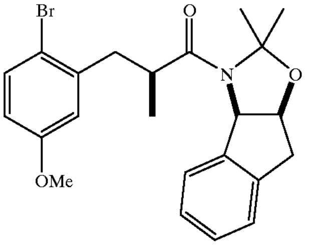

22

Preparation of 22

21 (MW 245.32, 1.1 equ, 89.1 g) in 1 L THF, cooled to −50° C. Add lithium bis(trimethylsilyl)amide (LiHMDS) (1.0 M in THF, 1.5 equ, 545 mL) and age 1.5 h, warming to −30° C. Add 20 (MW 279.96, 327 mmol, 91.3 g) in 300 mL THF, and age −35° C. for 1 h. Warm to −10° C. over 1 h, then quench into aqueous $NH_4Cl$. Separate layers and extract with ethyl acetate. Dry organic and concentrate in vacuo to afford crude 22 (MW 444.37).

EXAMPLE 11

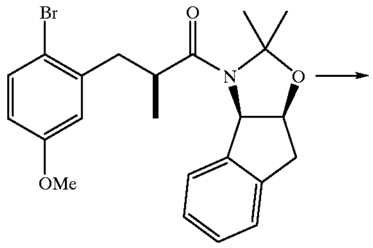

22

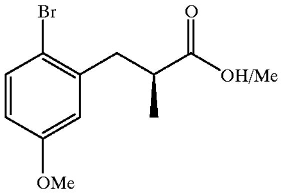

23

Preparation of 23

22 in 1 L MeOH and cooled to 10° C. Bubble in HCl gas for 1 h until reaction is complete. 2 L $H_2O$ added and the product was filtered. The cake was washed with $H_2O$ and dried to give the product hydroxyamide, which was then dissolved in 1 L MeOH and 1.5 L 6N HCl and refluxed overnight. The mixture was cooled to 25° C. and extracted with $CH_2Cl_2$ to give, after concentration, compounds 23 (60 g, 64% from bromide 20).

EXAMPLE 12

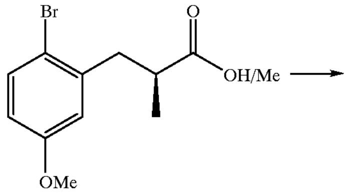

23

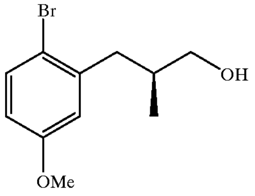

24

Preparation of 24

23 (mixture of acid and ester, 26.88 mmol) in 150 mL THF at −78° C. Add lithium aluminum hydride ($LiAlH_4$) (1 M in THF, 2 equ, 53.76 mL) over 30 min. Warm to 25° C. over 1 h, then quench into aqueous $NH_4Cl$. Add ethyl acetate, extract ethyl acetate. Wash organics with brine, dry (magnesium sulfate), and concentrate in vacuo to afford 95% yield of 24 (MW 259.14, 6.62 g).

EXAMPLE 13

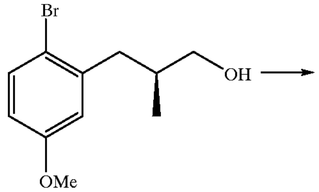

24

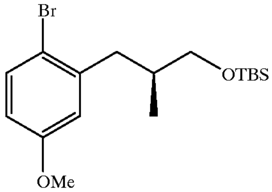

14

Preparation of 14

24 (MW 259.14, 25.54 mmol, 6.62 g) in 35 mL $CH_2Cl_2$ and cool to 0C. Add imidazole (MW 68.08, 2.5 equ, 4.35 g) and then tert-butyldimethylsilyl chloride (TBSCl) (MW 150.73, 1 equ, 3.85 g). Age 1 h at 25° C. then quench with aqueous $NaHCO_3$ and add ethyl acetate. Extract with ethyl acetate, then dry organic layer (magnesium sulfate) and concentrate in vacuo to afford a quantitative yield of 14 (MW 373.41, 9.54 g).

$^1$H NMR ($CDCl_3$) : 7.41 (d, J=8.74, 1H), 6.77 (d, J=3.04, 1H), 6.63 (dd, J=8.73, 3.06, 1H), 3.78 (s, 3H), 3.50 (d, J=5.75, 2H), 2.89 (dd, J=13.31, 6.15, 1H), 2.45 (dd, J=13.30, 8.26, 1H), 2.03 (m, 1H), 0.94 (s, 9H), 0.92 (d, J=5.01, 3H), 0.07 (s, 6H).

$^{13}$C NMR ($CDCl_3$) : 159.1, 141.6, 133.2, 117.0, 115.4, 113.2, 67.4, 55.4, 39.7, 36.3, 26.0 (3C), 18.4, 16.5, −5.3 (2C).

EXAMPLE 14

4

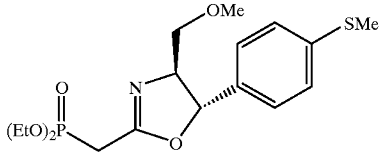

Preparation of 4

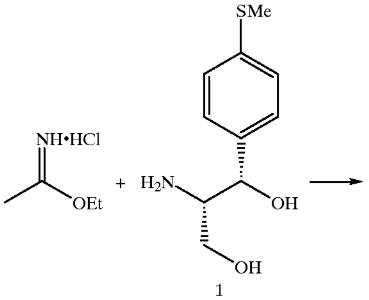

1

-continued

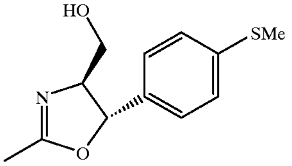

2

Step A: Preparation of 2

100 g (0.81 mols) of ethylacetimidate hydrochloride and 173 g (0.81 mols) of (S,S)-thiomicamine 1 were combined in 1 L of $CH_2Cl_2$ and stirred at room temperature overnight. The reaction was then quenched with water and extracted with $CH_2Cl_2$. The organic phase was dried over $MgSO_4$, filtered, and concentrated under reduced pressure. Recrystallization was accomplished using 700 mL of hot acetonitrile. Crystallization began at about 40° C. The solution was cooled to room temperature (about 20° C.) then cooled to 15° C. The resulting crystals were collected by vacuum filtration and air-dried over night to afford 134.5 g (70%) of the product, compound 2.

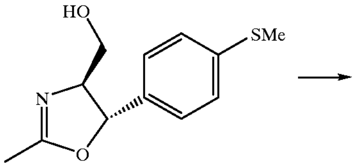

2

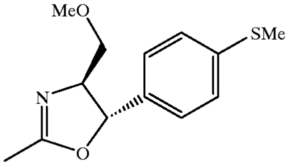

3

Step B: Preparation of 3

51.1 g (215 mmol) of compound 2 were dissolved in 1L of THF and cooled to 0° C. 24.7 g (224 mmol) of sodium t-pentoxide was then added. The mixture was aged at 0–5° C. for about 30 mins. 13.9 mL (224 mmol) of MeI were then added dropwise and the solution allowed to warm to room temperature. After 4 hours, the reaction was quenched with water and extracted with ethylacetate. The organic layer was dried over $MgSO_4$, filtered and concentrated under reduced pressure to yield 54.04 g (100%) of crude product 3.

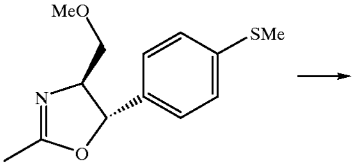

3

-continued

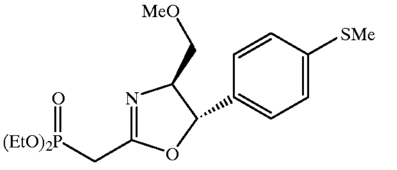

4

Step C: Preparation of Compound 4

132 mL (946 mmol) of diisopropylamine were dissolved in 200 mL THF and cooled to −21° C. 420 mL (946 mmol) of nBuLi (2.25 M in hexanes) were then added. The mixture was aged at −30 to −45° C. for about 40 minutes. The mixture was then cooled to −78° C. and 108 g (430 mmol) of compound 3 in 200 mL of THF were added dropwise while maintaining an internal temperature of about −70° C. After an additional 40 minutes, 66.5 mL (460.1 mmol) of diethylchlorophosphate were added neat. The solution was then allowed to warm to −10° C., quenched with water, and extracted with ethylacetate. The organic layer was dried over $MgSO_4$, filtered, and concentrated under reduced pressure to yield 166.11 g (99%) of the crude product 4.

EXAMPLE 15

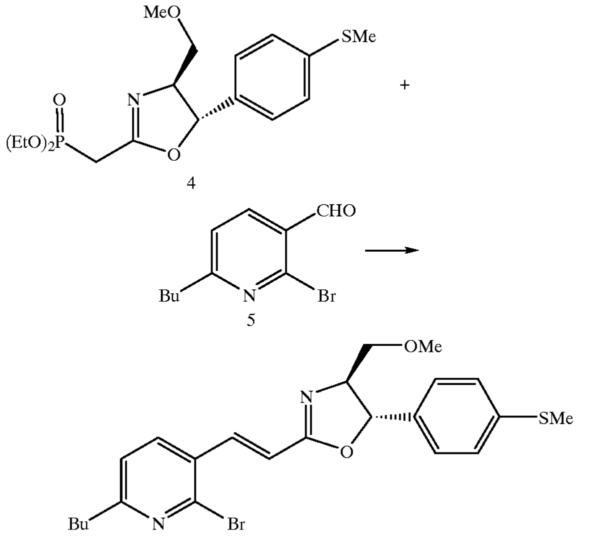

4

5

6

Preparation of 6

83.3 g (215 mmol) of compound 4 were dissolved in 1 L THF and cooled to −15° C. 90.3 mL (226 mmol) of nBuLi (2.5 M in hexanes) were then added dropwise while maintaining an internal temperature under 0° C. After 15 minutes, 41.6 g (172 mmol) of 2-bromo-6-butyl-3-pyridinecarboxaldehyde in 70 mL of THF were added dropwise while maintaining an internal temperature between −5° C. and 0° C. After 30 minutes at about −5° C., approximately 13% of the phosphonate ester still remained unreacted. Another 6.7 g (28 mmol) of the aldehyde was then added in THF at 0° C. After another 20 minutes, 4 to 5% of the phosphonate ester remained. An additional 0.27 g (1.12 mmols) of the aldehyde were added. After 30 minutes, the reaction was quenched with water and extracted with ethylacetate. The organic layer was dried over $MgSO_4$, filtered, and concentrated under reduced pressure to yield the crude product 6.

EXAMPLE 16

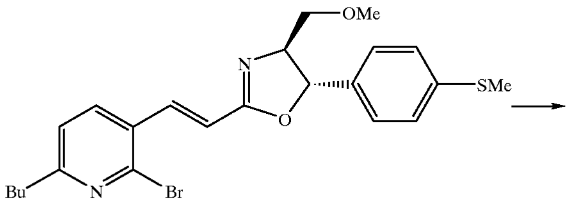

6

-continued

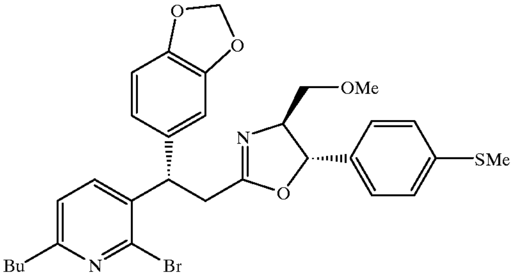

8

Preparation of 8

107.6 mL (893 mmol) of 4-bromo-1,2-(methylenedioxy)-benzene were dissolved in 2 L THF and cooled to −78° C. 357 mL (893 mmol) of nBuLi (2.5 M in hexanes) were then added dropwise while maintaining an internal temperature below −72° C. 202 g (425 mmol) of the product from Example 24 in 300 mL THF were added dropwise while maintaining an internal temperature below −70° C. After 30 minutes, the reaction was quenched with methanol at −70° C. and allowed to warm to −10° C. Saturated aqueous NaHCO3 was added and the phases separated. The aqueous layer was filtered through celite and extracted with ethylacetate. The ethylacetate layer was then dried over $MgSO_4$, filtered, and concentrated under reduced pressure to afford 320 g of the crude product 8.

1H NMR δ(ppm) 0.92 (3H, t); 1.35 (2H,m); 1.68 (2H,m); 2.46 (3H,s); 2.75 (2H,m); centered at 3.05 (2H,dd,dd); centered at 3.4 (2H,dd,dd); 3.34 (3H,s); 3.96 (1H,m); 4.87 (1H, t); 5.18 (1H,d); 5.92 (2H,s); 6.71–6.79 (3H, aromatic multiplet); 6.81–6.88 (2H, aromatic multiplet); 7.09–7.18 (3H, aromatic multiplet), 7.64 (1H,d).

EXAMPLE 17

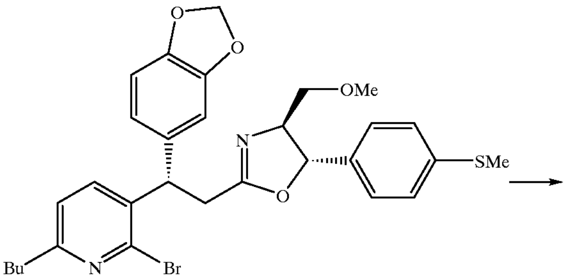

8

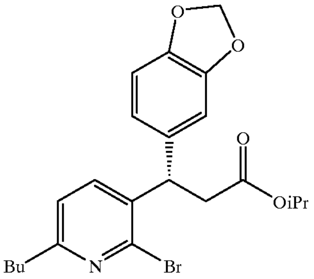

9

Preparation of 9

To a solution of 47.6 g (79.6 mmol) of 8 in 200 mL of isopropanol was added 44 mL of concentrated $H_2SO_4$ (18 M). The mixture was then heated to reflux. After 2.5 hours, the mixture was cooled to room temperature and diluted with water. The mixture was then extracted with ethylacetate and washed with a saturated aqueous solution of $NaHCO_3$. The organic phase was concentrated under reduced pressure and the residue dissolved in tert-butyl methyl ether. The ethereal solution was washed with 1N aqueous HCl and with a saturated aqueous solution of $NaHCO_3$. The organic layer was then dried over $MgSO_4$, filtered and concentrated under reduced pressure. The crude product was purified by column chromatography using a solvent gradient of 10:1 hexane/ethylacetate to 5:1 hexane/ethylacetate to afford 25.15 g (70%) of product 9.

$^1$H NMR δ(ppm) 0.91 (3H, triplet); 1.07 (3H, d); 1.13 (3H,d); 1.35 (2H, m); 1.65 (2H,m); 2.71 (2H,m); 2.93 (2H,m); 4.7–4.96 (2H, overlapping multiplets); 5.96 (2H,s); 6.72 (3H, aromatic multiplet); 7.05 (1H,d), 7.43 (1H,d).

EXAMPLE 18

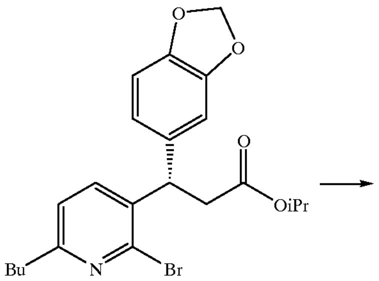

9

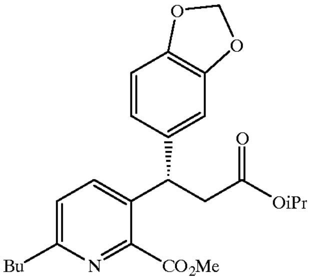

10

Preparation of 10

To a solution of 2 g (3.9 mmol) of 9, 66 mg (0.12 mmol) of DPPF (1,1'-bis(diphenylphosphino)-ferrocene) and 67 mg (8 mmol) of $NaHCO_3$ in 20 mL of methanol was added 27 mg (0.12 mmol) of palladium diacetate. The mixture was heated at 70° C. under 40 psi of carbon monoxide for 12 hours. The mixture was then cooled, concentrated under reduced pressure, and partitioned between ethylacetate and water. The aqueous layer was extracted with ethylacetate and the combined organic layers were dried over $MgSO_4$. The organic solvent was removed under reduced pressure to afford 1.56 g (94%) of the crude product 10

$^1$H NMR δ(ppm): 0.9(3H,t); 1.06(6H,d); 1.37(2H,m); 1.66(2H,m); 2.78(2H,m); 2.93(2H,m); 3.94(3H,s); 4.89(1H, m); 5.13(1H,t); 5.88(2H,s); 6.67–6.75(3H, aromatic multiplet); 7.2(1H,d); 7.56(1H,d).

EXAMPLE 19

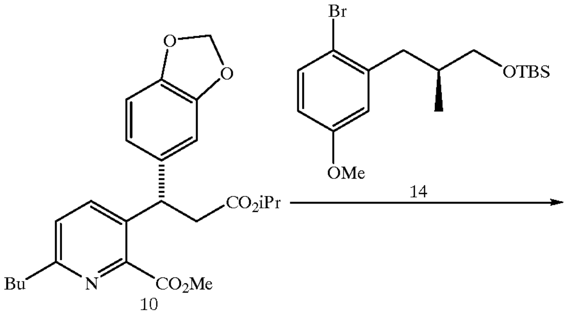

10

-continued

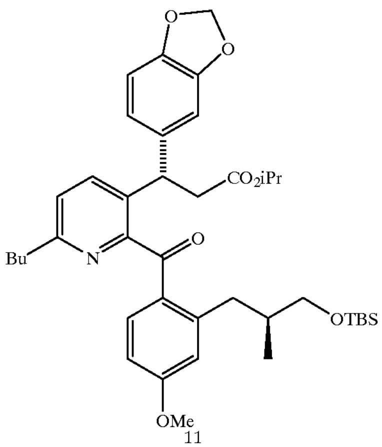

11

-continued

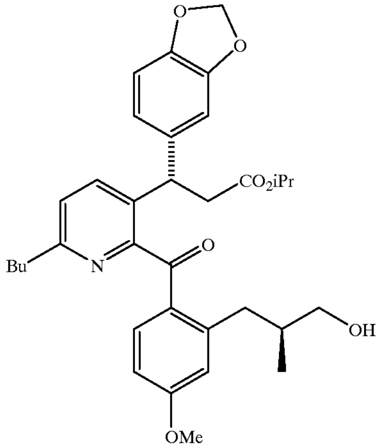

11A

Preparation of 11

To a solution of 2.62 g (7.02 mmol) of the arylbromide 14 in 15 mL THF was added 3.3 mL (7.1 mmol) of nBuLi (2.15 M in hexanes) while maintaining an internal temperature below −70° C. After 10 minutes, the solution was transferred via cooled cannula (dry ice) to a solution of the diester 10 in 35 mL of THF. The solution was observed to turn a green-black color. The mixture was stirred for an additional 0.5 hours and then quenched with aqueous $NaHCO_3$. The aqueous layer was extracted with ethylacetate (2×) and the combined organic layers dried over $MgSO_4$. Column chromatography using a 6:1 hexane/ethylacetate solvent system afforded 2.0 g (62%) of product 11 as a yellow oil.

1H NMR δ(ppm): 0.08(6H,s); 0.88(3H,t); 0.92(9H,s); 0.98(3H,d); 1.05(6H,d); 1.32(2H,m); 1.62(2H,m); 2.11(1H, dd); 2.72(2H,m); 2.93(2H,m); 3.12(1H,dd); 3.51(1H,dd); 3.62(1H,dd); 3.83(3H,s); 4.66(1H,t); 4.87(1H,m); 5.82(2H, m); 6.5–6.63(4H, aromatic multiplets); 6.81(1H,m); 7.02 (1H,d); 7.13(1H,d); 7.58(1H,d).

Preparation of 11A

To a solution of 0.8 g (1.16 mmol) of the silyl ether 11 in 20 mL acetonitrile at room temperature was added 0.5 mL og aqueous HF. After 10 minutes, the reaction was quenched with aqueous $NaHCO_3$ and extracted with ethylacetate (2×). The organic layer was dried over $MgSO_4$, filtered, and concentrated under reduced pressure to afford 0.66 g (99%) of the desilylated product 11A as a yellow foam.

1H NMR (300 MHz) δ0.8 (t, 3H), 0.95 (d, 3H), 1.00 (m, 6H), 1.25 (m, 3H), 1.55 (m, 2H), 2.00 (m, 1H), 2.77 (m, 3H), 2.90 (m, 1H), 3.16 (m, 1H), 3.40 (m, 2H), 3.75 (s, 3H), 4.55 (t, 1H), 4.81 (m, 1H), 5.76 (m, 2H), 6.50 (m, 4H), 6.74 (bs, 1H), 6.89 (d, 1H), 7.43 (d, 1H), 7.85 (d, 1H).

EXAMPLE 20

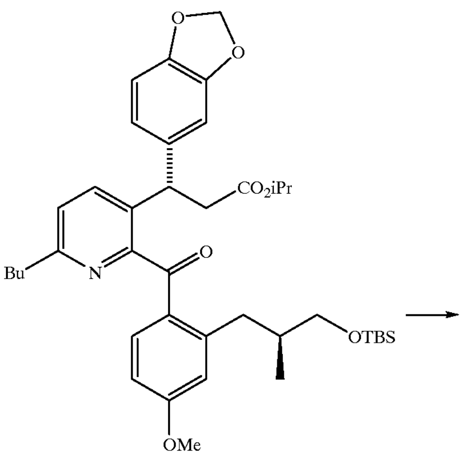

11

EXAMPLE 21

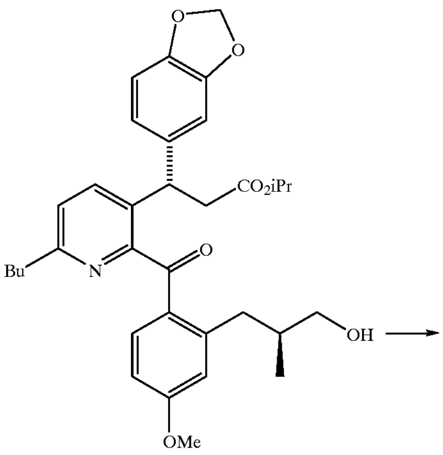

11A

-continued

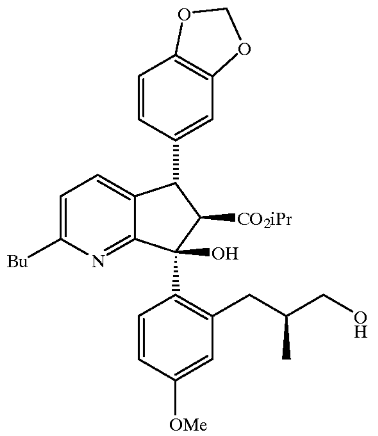

12

-continued

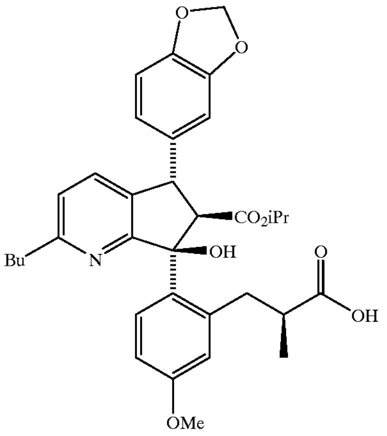

13a

Preparation of 12

0.21 g (0.37 mmol) of compound 11A were dissolved in 5 mL THF and cooled to −10° C. 0.12 g (1.1 mmol) of sodium t-pentoxide were then added as a solid and the reaction allowed to warm to room temperature. The reaction was subsequently quenched with 1N aqueous HCl and extracted with ethylacetate (2×). The organic layer was dried over $MgSO_4$, filtered, and concentrated under reduced pressure to afford 0.21 g (100%) of the crude cyclized product 12.

1H NMR (300 MHz) δ0.8 (m, 2H), 0.89 (t, 3H), 1.03 (d, 3H), 1.17 (m, 6H), 1.32 (m, 2H), 1.61 (m, 2H), 2.11 (m, 1H), 2.29 (m, 1H), 2.82 (m, 2H), 3.15 (m, 1H), 3.30 (m, 1H), 3.49 (d, 1H), 3.78 (t, 3H), 5.11 (m, 2H), 5.93 (s, 2H), 6.78 (m, 6H), 7.25 (d, 1H), 7.58 (d, 1H).

Preparation of 13a

To a solution of dihydroxy ester (4.2 g), 12 in acetone (20 ml) at −15 ° C. was added Jones reagent (8.4 ml) over a period of 1 h. The reaction was aged 0.5 h, warmed to 0° C. and quenched with water. The phases were separated and the aqueous phase was extracted with MTBE (2×10 ml). The organic phase was concentrated to a tan solid 13a and the crude material was carried directly to the deoxygenation reaction.

$^1H$ NMR (300 MHz) δ0.85 (t, 3H), 1.08 (m, 9H), 1.39 (m, 2H), 1.52 (m, 2H), 2.54 (m, 1H), 2.69 (m, 2H), 3.65 (m, 2H), 3.73 (s, 3H), 4.83 (m, 1H), 5.02 (m, 1H), 5.97 (s, 2H), 6.75 (m, 6H), 7.10 (d, 1H), 7.43 (d, 1H).

EXAMPLE 22

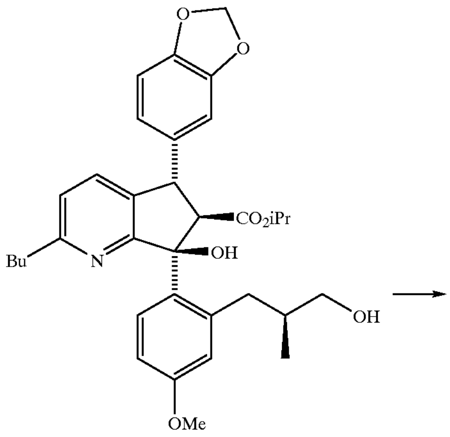

12

EXAMPLE 23

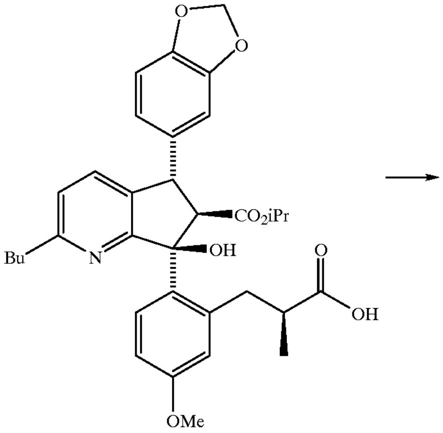

13a

-continued

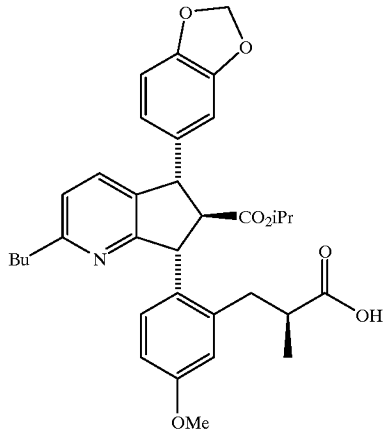

13b

Preparation of 13b

To a solution of 1.0 g (1.7 mmol) of compound 13a, from Example 22 in 10 mL of tetrahydrofuran (THF) was added 51 mL (5.1 mmol) of $SmI_2$ (0.1 M in THF) at room temperature. After 15 minutes, the reaction was quenched with 1N aqueous HCl and extracted with ethyl acetate twice. The organic layers were dried over $MgSO_4$, filtered and concentrated under reduced pressure to afford 0.98 g (100%) of the crude product 13b as a single diastereomer by $^1H$ NMR.

$^1H$ NMR (300 MHz) δ0.85 (t, 3H), 1.05 (d, 3H), 1.13 (m, 2H), 1.15 (d, 3H), 1.3 (d, 3H), 1.5 (m, 2H), 2.65 (m, 2H), 2.95 (m, 2H), 3.35 (dd, 1H), 3.52 (t, 1H), 3.72 (t, 3H), 4.55 (d, 1H), 5.00 (d, 1H), 5.90 (s, 2H), 6.75 (m, 5H), 6.95 (d, 1H), 7.08 (d, 1H), 7.37 (d, 1H).

What is claimed is:

1. A process for the preparation of a compound of Formula I

I

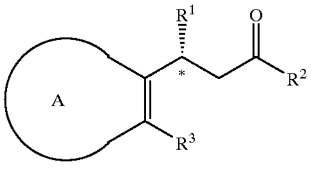

and the sterioisomer with opposite stereochemistry at C*, wherein

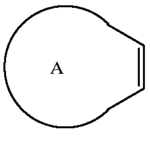

represents:

a) 6-membered heterocyclyl, wherein heterocyclyl is defined as pyridyl, and the pyridyl is unsubstituted or substituted with one, two or three $R^{10}$ substituents, wherein $R^{10}$ is selected from the group consisting of: OH, $CO_2R^4$, Br, Cl, F, I, $CF_3$, $N(R^5)_2$, $C_1$–$C_8$ alkoxy as defined below, $C_1$–$C_8$ alkyl as defined below, $C_2$–$C_8$ alkenyl as defined below, $C_2$–$C_8$ alkynyl as defined below, $C_3$–$C_8$ cycloalkyl as defined below, $CO(CH_2)_nCH_3$, and $CO(CH_2)_nCH_2N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, are unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_3$–$C_8$ cycloalkyl, $CO(CH_2)_nCH_3$, and $CO(CH_2)_nCH_2N(R^5)_2$, $R^1$ is:

a) aryl, aryl is defined as phenyl or naphthyl, which is unsubstituted or substituted with one, two or three substituents selected from the group consisting of: OH, OBenzyl, $CO_2R^4$, Br, Cl, F, I, $CF_3$, $N(R^5)_2$, $C_1$–$C_8$ alkoxy as defined above, $C_1$–$C_8$ alkyl as defined above, $C_2$–$C_8$ alkenyl as defined above, $C_2$–$C_8$ alkynyl as defined above, $C_3$–$C_8$ cycloalkyl as defined above, $CO(CH_2)_nCH_3$, $CO(CH_2)_nCH_2N(R^5)_2$, and when two substituents are located on adjacent carbons they can join to form a 5-membered methylenedioxy ring which is unsubstituted or substituted with one, two or three substituents selected from the group consisting of: H, OH, $CO_2R^6$, Br, Cl, F, I, $CF_3$, $N(R^7)_2$, $C_1$–$C_8$ alkoxy as defined above, $C_1$–$C_8$ as defined above, $C_2$–$C_8$ alkenyl as defined above, $C_2$–$C_8$ alkynyl as defined above, $C_3$–$C_8$ cycloalkyl as defined above, $CO(CH_2)_nCH_3$, and $CO(CH_2)_nCH_2N(R^5)_2$, or b) $C_1$–$C_8$ alkyl;

$R^2$ is:

a) $OR^4$, b) $N(R^5)_2$, c) OH; or $R^3$ is:

a) $C_1$–$C_8$ alkyl as defined above, b) $C_1$–$C_8$ alkoxy as defined above, c) aryl as defined above, d) $C(OR^a)(OR^b)$, wherein $R^a$ and $R^b$ are independently $(C_1$–$C_5)$alkyl and may be connected to form a 5- or 6-membered heterocyclic ring containing two oxygens, or e) CHO;

n is: 0 to 5;

$R^4$ is $C_1$–$C_8$ alkyl as defined above;

$R^5$ is H, $C_1$–$C_8$ alkyl as defined above, or aryl as defined above;

$R^6$ is H, $C_1$–$C_8$ alkyl as defined above, or aryl as defined above; and $R^7$ is H, $C_1$–$C_8$ alkyl as defined above, or aryl as defined above, when there are two $R^7$ substituents on a nitrogen they can join to form a 3- through 6-membered ring, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy as defined above, $C_1$–$C_8$ alkyl as defined above, $C_2$–$C_8$ alkenyl as defined above, $C_2$–$C_8$ alkynyl as defined above, $C_3$–$C_8$ cycloalkyl as defined above, $CO(CH_2)_nCH_3$, and $CO(CH_2)_nCH_2N(R^5)_2$;

comprising the steps of:

1) reacting a vinyl-substituted, chiral oxazoline of Formula II

II

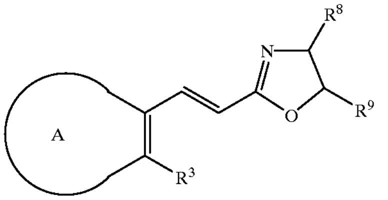

wherein $R^8$ and $R^9$ are independently:

a) aryl, wherein aryl is as defined in $R^1$(a) above, b) heteroaryl, wherein heteroaryl is defined as a 5- or 6-membered aromatic ring containing 1, 2 or 3 heteroatoms selected from O, N and S, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, $C_3$–$C_8$ cycloalkyl, $CO(CH_2)_nCH_3$, and $CO(CH_2)_nCH_2N(R^5)_2$, c) $CH_2OR^4$, d) aryl-$SCH_3$, wherein aryl is as defined in $R^1$(a) above, e) $C_1$–$C_8$ alkyl, or f) H, so long as both $R^8$ and $R^9$ are not both H at the same time; with an amount of an organolithium compound, $R^1$Li, in an aprotic solvent at a temperature between about −100° to about 25° C. to produce a chiral adduct; and 2) hydrolyzing the chiral adduct with a hydrolyzing reagent to produce a compound of Formula I.

2. The process as recited in claim 1, step 1, wherein the amount of the organolithium compound is between about 1 to about 4 equivalents relative to the chiral oxazoline.

3. The process as recited in claim 2, wherein the aprotic solvent used is chosen from a group consisting of tetrahydrofuran, diethyl ether, MTBE (methyl t-butyl ether), benzene, toluene, pentane, hexane, dioxane and a mixture of said solvents.

4. The process as recited in claim 1, step 2, wherein the hydrolyzing reagent is chosen from a group of electrophilic reagents consisting of $H_2SO_4$, $H_2NO_3$, HCl, acetic acid, trifluoroacetic acid, $TiCl_4$, $BF_3$, $BCl_3$, $SnCl_4$, $AlCl_3$, $TiCl_2(OiPr)_2$, methyl iodide, methyl triflate, ethyl iodide, ethyl triflate and triflic anhydride.

5. The process as recited in claim 1, step 1, wherein the amount of the organolithium compound is between about 2 to about 3 equivalents relative to the chiral oxazoline.

6. The process as recited in claim 5 wherein the aprotic solvent is tetrahydrofuran.

7. The process as recited in claim 6 wherein the hydrolyzing reagent in step 2 is $H_2SO_4$.

8. A process for the preparation of a compound of Formula II:

II

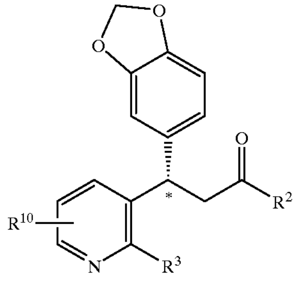

and the sterioisomer with opposite stereochemistry at C*, wherein $R^2$ is:

a) $OR^4$, b) $N(R^5)_2$, c) or OH;

$R^3$ is:

a) H, b) $C_1$–$C_8$ alkyl, c) $C_1$–$C_8$ alkoxy, d) Br, Cl, F, I, e) aryl, aryl is defined as phenyl or naphthyl, which is unsubstituted or substituted with one, two or three substituents selected from the group consisting of: OH, OBenzyl, $CO_2R^4$, Br, Cl, F, I, $CF_3$, $N(R^5)_2$, $C_1$–$C_8$ alkoxy, $C_1$–$C_8$, $C_2$–$C_8$ alkenyl, $C_2$–$C_8$ alkynyl, $C_3$–$C_8$ cycloalkyl, $CO(CH_2)_nCH_3$, $CO(CH_2)_nCH_2N(R^5)_2$, and when two substituents are located on adjacent carbons they can join to form a 5-membered methylenedioxy ring which is unsubstituted or substituted with one, two or three substituents selected from the group consisting of: H, OH, $CO_2R^6$, Br, Cl, F, I, $CF_3$, $N(R^7)_2$, $C_1$–$C_8$ alkoxy, $C_1$–$C_8$ alkyl, $C_2$–$C_8$ alkenyl, $C_2$–$C_8$ alkynyl, $C_3$–$C_8$ cycloalkyl, $CO(CH_2)_nCH_3$, and $CO(CH_2)_nCH_2N(R^5)_2$, f) heteroaryl, heteroaryl is defined as a 5- or 6-membered aromatic ring containing 1, 2 or 3 heteroatoms selected from O, N and S, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, $C_3$–$C_8$ cycloalkyl, $CO(CH_2)_nCH_3$, and $CO(CH_2)_nCH_2N(R^5)_2$, or g) $C(OR^a)(OR^b)$, wherein $R^a$ and $R^b$ are independently $(C_1$–$C_5)$alkyl and may be connected to form a 5- or 6-membered heterocyclic ring containing two oxygens;

$R^4$ is $C_1$–$C_8$ alkyl;

$R^5$ is H, $C_1$–$C_8$ alkyl or aryl;

comprising the steps of:

(1) reacting a vinyl-substituted, chiral oxazoline of Formula VII

VII

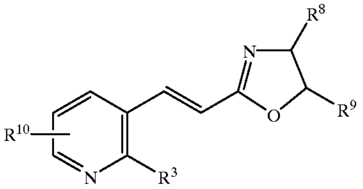

wherein $R^8$ and $R^9$ are independently:

a) aryl, wherein aryl is as defined in $R^3$(e) above, b) heteroaryl, wherein heteroaryl is as defined in $R^3$(f) above, c) $CH_2OR^4$, d) aryl-$SCH_3$, wherein aryl is as defined in $R^3$(e) above, e) $C_1$–$C_8$ alkyl, or f) H, so long as both $R^8$ and $R^9$ are not both H at the same time; and $R^{10}$ is:

a) OH, b) $CO_2R^4$, c) halo, wherein halo is Br, Cl, F, or I, d) $CF_3$, e) $N(R^5)_2$, f) $C_1$–$C_8$ alkoxy, g) $C_1$–$C_8$ alkyl, h) $C_2$–$C_8$ alkenyl, i) $C_2$–$C_8$ alkynyl, j) $C_3$–$C_8$ cycloalkyl, k) $CO(CH_2)_nCH_3$, or l) $CO(CH_2)_nCH_2N(R^5)_2$;

with an amount of an organolithium compound of Formula VIII

VIII

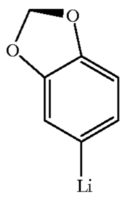

in an aprotic solvent at a temperature between about −78° and 0° C. to produce a chiral adduct; and (2) hydrolyzing the chiral adduct with a hydrolyzing reagent to produce a compound of Formula II.

9. The process as recited in claim 8, step 1, wherein the amount of the organolithium compound of Formula VIII is between about 2 to about 3 equivalents relative to the chiral oxazoline.

10. The process as recited in claim 9 wherein the aprotic solvent used is chosen from a group consisting of tetrahydrofuran, diethyl ether, MTBE (methyl t-butyl ether), benzene, toluene, pentane, hexane, dioxane and a mixture of said solvents.

11. The process as recited in claim 8, step 2, wherein the hydrolyzing reagent is $H_2SO_4$.

* * * * *